United States Patent

Tenud

[11] 3,969,406
[45] July 13, 1976

[54] PROCESS FOR THE PRODUCTION OF CARNITINE

[75] Inventor: Leander Tenud, Visp, Vs, Switzerland

[73] Assignee: Lonza Ltd., Gampel, Switzerland

[22] Filed: Apr. 28, 1975

[21] Appl. No.: 572,316

[30] Foreign Application Priority Data

Apr. 26, 1974  Switzerland.................. 5730/74

[52] U.S. Cl. .................... 260/534 M; 260/562 N
[51] Int. Cl.² ........................................ C07C 101/30
[58] Field of Search ........................... 260/534 M

[56] References Cited
UNITED STATES PATENTS

| | | | |
|---|---|---|---|
| 2,328,021 | 8/1943 | Katzman et al. | 260/534 M |
| 2,530,627 | 11/1950 | Pfister et al. | 260/534 M |
| 2,571,755 | 10/1951 | Pfister et al. | 260/534 M |
| 3,038,007 | 6/1962 | Reeve | 260/534 M |
| 3,096,368 | 7/1963 | Binon et al. | 260/534 M |
| 3,135,788 | 6/1964 | Noguchi et al. | 260/534 M |
| 3,462,485 | 8/1969 | Binon et al. | 260/534 M |

FOREIGN PATENTS OR APPLICATIONS 39-24880  1964  Japan .......................... 260/534 M

*Primary Examiner*—Joseph E. Evans
*Attorney, Agent, or Firm*—Virgil H. Marsh; Arnold B. Christen

[57] ABSTRACT

The process for the production of carnitine hydrochloride which includes reacting a α-haloacetoacetanilide having the formula:

$$XCH_2COCH_2CONYC_6H_5$$

where X is a halogen atom and Y is a hydrogen atom, a phenyl group, a benzyl group or an alkyl group having 1 to 8 carbon atoms, with trimethylamine, a γ-trimethylammonium acetoacetanilide halide resulting. The γ-trimethylammonium acetoacetanilide halide, is hydrogenated, a γ-trimethylammonium-β-hydroxybutyric acid halide resulting. The γ-trimethylammonium-β-hydroxybutyric acid halide is converted by means of aqueous hydrochloric acid into the carnitine hydrochloride.

9 Claims, No Drawings

PROCESS FOR THE PRODUCTION OF CARNITINE

BACKGROUND OF THIS INVENTION

1. Field of This Invention

This invention relates to a process for the production of carnitine hydrochloride.

2. Prior Art

It is known to produce carnitine from acetoacetic ester. At the same time the bromoacetoacetic ester is produced by bromation, the latter is converted by means of $NaBH_4$ to the $\beta$-hydroxy-$\alpha$-bromobutyric acid ester. The latter is reacted with trimethylamine and the developing $\alpha$-trimethylammonium-$\beta$-hydroxybutyric acid ester bromide is saponified into carnitine hydrochloride [F. D'Alo and A. Masserini, Chemical Abstracts, Vol. 60, 10777 g (1964)]. Because of the reduction with sodiumborohydride, this synthesis will probably remain limited for economic reasons merely to the laboratory scale; moreover the yields are low.

It is known to use epichlorohydrin as a starting material. In such case, one proceeds in such a way that epichlorohydrin is first of all reacted with trimethylaminehydrochloride, the reaction product is converted with NaCN into the carnitine nitrile chloride and the latter is hydrolyzed to carnitine (see U.S. Pat. No. 3,135,788). In such process the products of all the intermediate steps are isolated. The yield amounts to about 74 percent.

BROAD DESCRIPTION OF THIS INVENTION

It is an object of this invention to produce carnitine hydrochloride at a good yield by means of a multi-step process that does not require isolation of the products of the intermediate steps of such process. Other objects and advantages of this invention are set out herein or are obvious to one ordinarily skilled in the art herefrom. This invention achieves such objects and advantages.

This invention includes a process for the production of carnitine hydrochloride. The process includes reacting a $\gamma$-haloacetoacetanilide having the formula:

where X is a halogen atom and Y is a hydrogen atom or an alkyl group having 1 to 8 carbon atoms, with trimethylamine, a $\gamma$-trimethylammonium acetoacetanilide halide resulting. The $\gamma$-trimethylammonium acetoacetanilide halide, is hydrogenated, a $\gamma$-trimethylammonium-$\beta$-hydroxybutyric acid halide resulting. The $\gamma$-trimethylammonium-$\beta$-hydroxybutyric acid halide is converted by means of aqueous hydrochloric acid into carnitine hydrochloride.

In the process of this invention, it is not necessary to isolate the products of the intermediate steps.

Preferably the first reaction step and the hydrogenation step are conducted in the presence of an organic solvent or suspension agent or of water. Preferably the first reaction step is conducted at a temperature between 20° and 70°C. Preferably the hydrogenation step is conducted catalytically, and preferably the catalyst is platinum and/or activated charcoal. Preferably the hydrogenation step is conducted at a $H_2$-pressure between 5 and 70 atmospheres. Preferably the hydrogenation step is conducted at a temperature between 0° and 50°C.

DETAILED DESCRIPTION OF THIS INVENTION

Carnitine hydrochloride is:

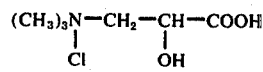

Useful $\gamma$-haloacetoacetanilides are the $\gamma$-bromoacetoacetanilides and the $\gamma$-chloroacetoacetanilides (preferred). $\gamma$-haloacetoacetanilides includes derivatives, such as, $\gamma$-haloacetoacetalkylanilides, $\gamma$-haloacetoacetbenzylanilides, $\gamma$-haloacetoacetphenylanilides. Useful $\gamma$-haloacetoacetalkylanilides are those having 1 to 8 carbon atoms in the alkyl group-examples thereof are $\gamma$-bromoacetoacet-N-ethylanilide, $\gamma$-bromoacetoacet-N-methylanilide, $\gamma$-bromoacetoacet-N-octylanilide, $\gamma$-bromoacetoacet-N-isopropylanilide, $\gamma$-bromoacetoacet-N-butylanilide, $\gamma$-bromoacetoacet-N-pentylanilide, $\gamma$-chloroacetoacet-N-methylanilide, $\gamma$-chloroacetoacet-N-ethylanilide, $\gamma$-chloroacetoacet-N-pentylanilide, $\gamma$-chloroacetoace-N-octylanilide, $\gamma$-chloroacetoacet-N-heptylanilide, $\gamma$-chloroacetoacet-N-isobutylanilide and $\gamma$-chloroacetoacet-N-propylanilide. Examples of useful $\gamma$-haloacetoacetphenilides are $\gamma$-chloroacetoacetphenylanilide and $\gamma$-bromoacetoacetphenylanilide. Examples of useful $\gamma$-haloacetoacetbenzylanilides are $\gamma$-chloroacetoacetbenzylanilide and $\gamma$-bromoacetoacetbenzylanilide. The most preferred $\gamma$-haloacetoacetanilide is $\gamma$-chloroacetoacetanilide.

Preferably the reaction of the $\gamma$-haloacetoacetanilide with trimethylamine and the hydrogenation of the $\gamma$-trimethylammonium acetoacetanilide chloride are conducted in water or in an organic solvent or suspension agent. Examples of such organic solvents or suspension agents are methanol, ethanol, isopropanol, propanol, butanol, acetonitrile, dimethyl sulfoxide and dimethyl formamide.

The reaction of trimethylamine with the $\gamma$-haloacetoacetanilide is preferably done at a temperature between 20° and 70°C.

The hydrogenation is preferably carried out catalytically and most preferably using hydrogen and using platinum or activated charcoal as the catalyst.

The hydrogenation step is preferably conducted at a temperature from 0° to 50°C and a $H_2$ pressure of 5 to 70 atm.

The process of this invention is distinguished by the fact, that it is a so called "one course" process, that is to say the products of the individual steps do not need to be isolated. The yields which can be achieved according to the process of this invention lie at about 75 to 85 percent, or more.

By way of summary, this invention involves reacting $\gamma$-chlorocetoacetic acid anilide with trimethylamine to give a $\gamma$-trimethylammonium acetoacetic acid anilide chloride, which is hydrogenated to a $\gamma$-trimethylammonium-$\beta$-hydroxybutyric acid anilide chloride, which in turn is converted by means of aqueous hydrochloric acid into carnitine hydrochloride.

The following is a schematic of the reaction steps of this invention:

-continued
XCH$_2$COCH$_2$CONYC$_6$H$_5$ + N(CH$_3$)$_3$

↓

(CH$_3$)$_3$N—CH$_2$COCH$_2$CONYC$_6$H$_5$
|
X

↓ hydrogenation (CH$_3$)$_3$N—CH$_2$CHCH$_2$CONYC$_6$H$_5$
|             |
X            OH ↓ HCl
  H$_2$O (CH$_3$)$_3$N—CH$_2$CHCOOH
|             |
Cl           OH In this specification, including the claims, all parts, ratios, weights and proportions are on a weight basis, unless otherwise stated or unless otherwise obvious to one ordinarily skilled in the art.

EXAMPLE 1

12.82 gm (59.97 m mole) of γ-chloroacetoacetic acid anilide was suspended in a 100 ml 3-necked flask with a magnetic stirrer, thermometer and reflux cooler in 30 ml of methanol. 13.72 gm (71.95 m mole) of trimethylamine were dissolved in mixture. The reaction was conducted in methanol and was stirred for 6.5 hours at 50°C. After that, the mixture was transferred into a stirring autoclave and 1.3 gm. of platinum/activated charcoal and another 160 ml of methanol were added. At a stirring velocity of 750 rpm and a pressure of 40 atm. The mixture was hydrogenated for 6 hours at 40°C. The catalyst was filtered off. The filtrate was evaporated, 30 ml of water and 20 ml of concentrated hydrochloric acid were added and the mixture was heated during 3 hours to 100°C. The mixture was filtered and was evaporated until dry on a rota-vaporator at 80°C. After that, the mixture was reacted with 75 ml of isopropanol and 75 ml of ethanol, and then filtered. After standing for 1 hour in a refrigerator at 3° to 5°C, the crystals were filtered off. The crystals were washed with isopropanol and were dried in high vacuum. Subsequently a purification with activated charcoal in methanol was carried out, whereby carnitine hydrochloride was obtained by precipitation with ethanol-isopropanol. The carnitine hydrochloride had a melting point of 196.5° to 197°C. and the yield amounted to 77.5 percent.

EXAMPLE 2

Carnitine hydrochloride from γ-chloroacetoacetic-N-methylanilide in water 22.6 gm (0.10 mole) of γ-chloroacetoacetic acid-N-methylanilide was inserted into a solution of 7.09 gm. (0.12 mole) of trimethylamine in 60 ml of distilled water and were stirred at ambient temperature, whereby the educt was dissolved. After 6 hours, a homogenous product appeared on the thin layer plate. The excess trimethylamine was removed on a rota-vaporator. The reaction solution was hydrogenated in a laboratory autoclave over 2.4 gm. of 5 percent Pt/activated charcoal with the addition of 150 ml of distilled water during 6 hours at 10°C and 10 atm. of hydrogen pressure. The catalyst was filtered off. The filtrate was concentrated, was reacted with 35 ml of concentrated hydrochloric acid and was hydrolyzed during 3 hours at boiling temperature. The solution was filtered and was evaporated until dry in a rota-vaporator. The solid residue was suspended in 110 ml of ethanol at 0° to 5°C, whereby the N-methylaniline hydrochloride was dissolved and it was possible to filter off the carnitine hydrochloride. The crystalline product had a melting point of 197° to 198.5°C and was identical to an authentic sample. The yield was 82 percent, based on the γ-chloroacetoacetic acid-N-methylanilide.

EXAMPLE 3

Carnitine hydrochloride from γ-chloroacetoacetic anilide in water as solvent 12.82 gm. (59.97 m mole) of γ-chloroacetoacetic acid anilide were added to a solution of 4.25 gm. (71.95 m mole) of trimethylamine in 55 ml of distilled water and were stirred at ambient temperature, whereby the anilide was dissolved. After 5 to 6 hours, the sole presence of γ-trimethylammoniumacetoacetic anilide chloride appeared on the thin layer plate. The excess trimethyl amine was removed on a rota-vaporator. The reaction solution was hydrogenated in an SFS stirring autoclave over 1.3 gm. of 5 percent Pt/activated charcoal, while adding further 150 ml. of distilled water, during 6 hours at 10°C and 10 atm. of hydrogen pressure. The catalyst was filtered off. The filtrate was concentrated and 20 ml of concentrated hydrochloric acid were added. The mixture was heated to 100°C. during 3 hours. The mixture was filtered and evaporated on the rota-vaporator until dry at 80°C.

The solid residue was suspended in 60 ml of ethanol at 0° to 5°C., whereby the anilinehydrochloride was dissolved and the carnitinehydrochloride could be filtered off. The product had a melting point of 198° to 199°C and was identical to an authentic sample. The yield amounted to 84 percent, based on the γ-chloroacetoacetic anilide.

What is claimed is:
1. The process for the production of carnitine hydrochloride which comprises (a) reacting a γ-haloacetoacetanilide having the formula:

XCH$_2$COCH$_2$CONYC$_6$H$_5$ where X is a halogen atom and Y is a hydrogen atom or an alkyl group having 1 to 8 carbon atoms, with trimethylamine, a γ-trimethylammonium acetoacetanilide halide resulting, (b) hydrogenating said γ-trimethylammonium acetoacetanilide halide, a γ-trimethylammonium-β-hydroxybutyric acid halide resulting, and (c) converting said γ-trimethylammonium-β-hydroxybutyric acid halide by means of aqueous hydrochloric acid into said carnitine hydrochloride, which has the formula:

(CH$_3$)$_3$N—CH$_2$—CH—COOH.
|                    |
Cl                  OH

2. The process of claim 1 wherein said reaction step (a) is conducted in the presence of an organic solvent or suspension agent or of water.

3. The process of claim 1 wherein said reaction step (a) is conducted at a temperature between 20° and 70°C.

4. The process of claim 1 wherein said hydrogenation step (b) is conducted in the presence of an organic solvent or suspension agent or of water.

5. The process of claim 1 wherein said hydrogenation step is conducted catalytically.

6. The process of claim 5 wherein said catalyst is platinum or activated charcoal.

7. The process of claim 1 wherein said hydrogenation step (b) is conducted at a temperature between 0° and 50°C.

8. The process of claim 1 wherein said hydrogenation step (b) is conducted at a $H_2$ — pressure between 5 and 70 atmospheres.

9. The process of claim 1 wherein said reaction step (a) and said hydrogenation step (b) are conducted in the presence of an organic solvent or suspension agent or of water.

* * * * *